US011439935B2

(12) United States Patent
Langen et al.

(10) Patent No.: US 11,439,935 B2
(45) Date of Patent: Sep. 13, 2022

(54) DEVICE FOR THE SEPARATION OF FLUE GAS PARTICLES IN LAPAROSCOPY

(71) Applicant: W.O.M. WORLD OF MEDICINE GMBH, Berlin (DE)

(72) Inventors: Fabian Langen, Berlin (DE); Peter Juelg, Freiburg (DE)

(73) Assignee: W.O.M. World of Medicine GmbH, Berlin (DE)

( * ) Notice: Subject to any disclaimer, the term of this patent is extended or adjusted under 35 U.S.C. 154(b) by 205 days.

(21) Appl. No.: 16/477,945

(22) PCT Filed: Jan. 15, 2018

(86) PCT No.: PCT/DE2018/000007
§ 371 (c)(1),
(2) Date: Jul. 15, 2019

(87) PCT Pub. No.: WO2018/130243
PCT Pub. Date: Jul. 19, 2018

(65) Prior Publication Data
US 2019/0366251 A1  Dec. 5, 2019

(30) Foreign Application Priority Data
Jan. 13, 2017 (DE) .......................... 102017000219.3

(51) Int. Cl.
*B01D 53/06* (2006.01)
*B01D 45/16* (2006.01)
(Continued)

(52) U.S. Cl.
CPC ......... *B01D 45/16* (2013.01); *B01D 46/0036* (2013.01); *B01D 50/20* (2022.01);
(Continued)

(58) Field of Classification Search
CPC .. B01D 45/16; B01D 46/0036; B01D 50/002; B01D 53/0407; B01D 53/261; B01D 2253/102; B01D 2253/202; B01D 2259/4533; A16B 2218/008; B04C 2003/006; B04C 2009/002
See application file for complete search history.

(56) References Cited

U.S. PATENT DOCUMENTS 3,895,930 A * 7/1975 Campolong .............. B04C 3/00
                                                    55/394
4,255,174 A    3/1981 Simpson
(Continued)

FOREIGN PATENT DOCUMENTS

DE         2947737 A1     6/1980
EP         2832449 A1     2/2015
WO    WO-2014204195 A1 * 12/2014 ............. A61B 18/00

OTHER PUBLICATIONS

"Lee Chung Hee et al., Smoke Removal Filter, Published Dec. 2014" (Machine translation obtained from WIPO (Sep. 2021)) (Year: 2014).*

*Primary Examiner* — Dung H Bui
(74) *Attorney, Agent, or Firm* — Mayer & Williams, PC; Stuart H. Mayer

(57) ABSTRACT

Subject matter of the present invention is a device for the separation of flue gas particles and liquid droplets in the exhaustion of surgical gases during laparoscopic interventions.

17 Claims, 9 Drawing Sheets

(51) Int. Cl.
  *B01D 46/00*   (2022.01)
  *B01D 53/04*   (2006.01)
  *B01D 53/26*   (2006.01)
  *B01D 50/20*   (2022.01)
  *B04C 3/00*   (2006.01)
  *B04C 9/00*   (2006.01)

(52) U.S. Cl.
  CPC ....... *B01D 53/0407* (2013.01); *B01D 53/261* (2013.01); *A61B 2218/008* (2013.01); *B01D 2253/102* (2013.01); *B01D 2253/202* (2013.01); *B01D 2259/4533* (2013.01); *B04C 2003/006* (2013.01); *B04C 2009/002* (2013.01)

(56) References Cited

U.S. PATENT DOCUMENTS

| | | | |
|---|---|---|---|
| 5,460,602 | A | 10/1995 | Shapira |
| 5,968,032 | A | 10/1999 | Sleister |
| 6,524,307 | B1 | 2/2003 | Palmerton |
| 6,544,210 | B1 * | 4/2003 | Trudel ............ A61B 18/00 604/26 |
| 6,592,543 | B1 | 7/2003 | Wortrich |
| 2005/0172589 | A1 | 8/2005 | Gammelsaeter |
| 2011/0041468 | A1 | 2/2011 | Schultz |
| 2013/0152525 | A1 | 6/2013 | Brandner |
| 2014/0165842 | A1 | 6/2014 | Bonano |

* cited by examiner

Figure 7:
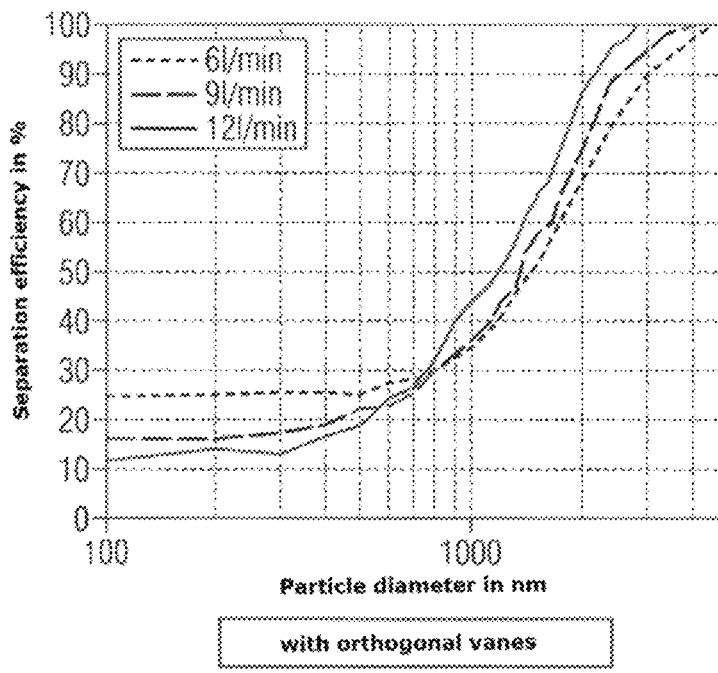
Fig. 7A
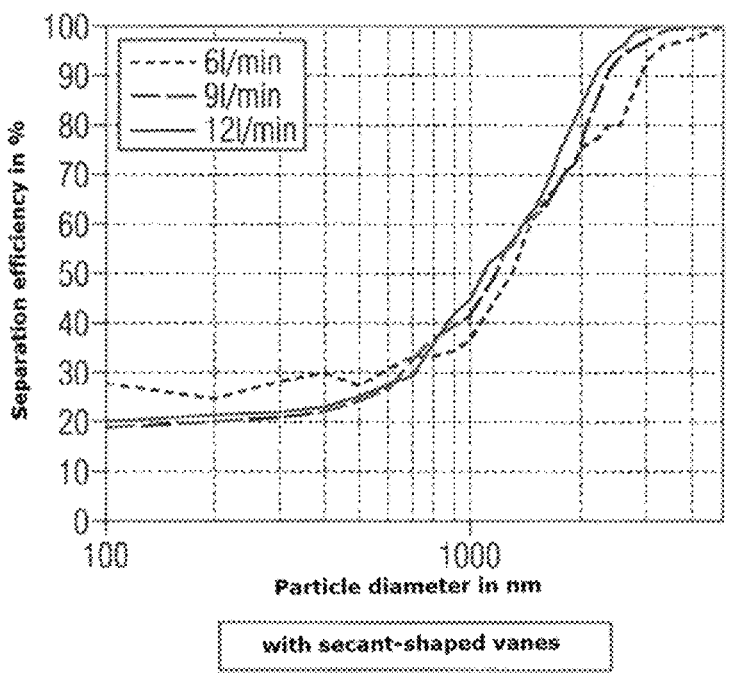
Fig. 7B

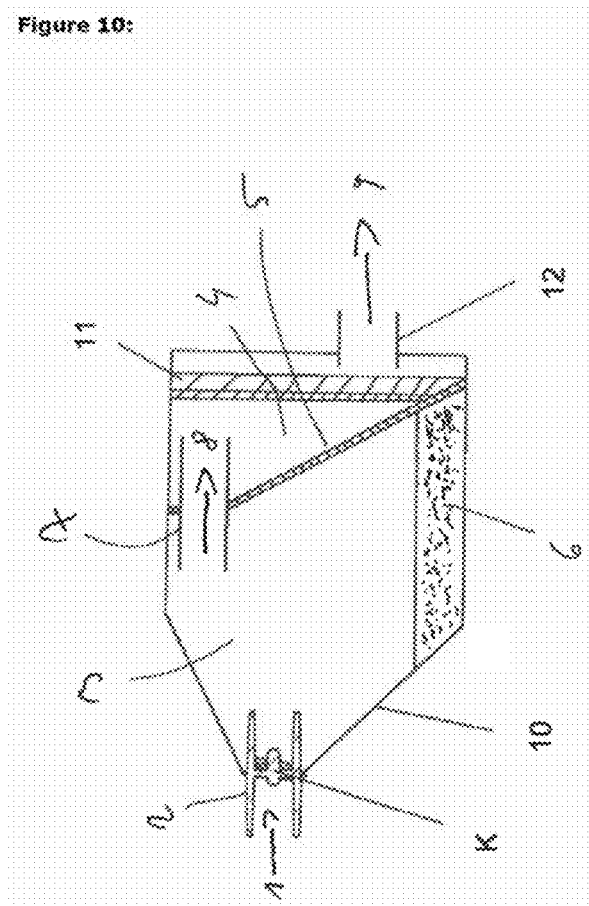

DEVICE FOR THE SEPARATION OF FLUE GAS PARTICLES IN LAPAROSCOPY

BACKGROUND OF THE INVENTION

Subject matter of the present invention is a device for the separation of flue gas particles, liquid droplets and humidity in the exhaustion of surgical gases during laparoscopic interventions.

Minimally invasive surgical techniques are becoming increasingly popular. When intra-operatively using laser scalpels or other electrical and ultrasonic surgical instruments in minimally invasive interventions, e.g. in laparoscopy, frequently flue gases develop within the patient's body. Such flue gases contain a complex mixture of particulate, droplet-like and gaseous components. Such flue gases must not escape, for safety reasons already, in an unfiltered condition into the operation room. Modern insufflators frequently include corresponding exhaust hoses and respective filter devices, by means of which flue gases produced in the patient's body can be filtered out. Usually, these are fiber filters or membranes filtering droplets and particles out. Such filters have various drawbacks: membranes are relatively easily clogged, fiber filter need a low flow rate in order to filter in an optimum way.

There is a need, therefore, to develop a device that effectively holds back droplets, humidity and particles from intra-operatively produced flue gases, without having the described drawbacks.

From large-scales installations, so-called cyclonic separators are known that have the task to separate larger particles or drops from gas flows. Examples are described in the documents U.S. Pat. No. 4,255,174, US 2013/0152525 A1, US 2005/0172589, and EP 2832449 A1.

The present invention provides a device that solves the above problems, in spite of its simplicity. It is a substantially tube-shaped unit that can be arranged, for instance, in the manner of a connector between two hose portions. The tubular device has guide vanes in its interior which confer a radial movement component to a fed-through gas flow. A laminar or turbulent gas flow fed through the device according to the invention is, after passing through the device, forwarded in a helical or spiral shape. By the generated centrifugal forces, droplets and particles are moved to the hose wall, where they are separated by adhesion. In addition, a pressure drop occurs during the passage through the device, which leads to a condensation of the liquids dissolved in the gas and thus to a formation of condensation.

SUMMARY OF THE INVENTION

Subject matter of the invention is, thus, a device for the separation of particles, droplets, and humidity from flowing flue gases with a flow rate of 3 to 20 l/min,
comprising a tube of length l of 10 to 50 mm, the tube having an inner diameter $d_i$ of 4 to 20 mm,
comprising an axially located flow body K having a web cross-section of 0.5 to 6 mm,
comprising two to six guide vanes L disposed between the axially located flow body K and the inner wall of the tube and being rigidly connected thereto,
wherein the guide vanes L are helically arranged so as to confer a radial movement component to the gas flowing through.

BRIEF DESCRIPTION OF THE DRAWINGS

FIGS. 7A and 7B show separation curves of the devices shown in FIG. 1 for different gas flows.

FIG. 10 shows the device integrated in a filter housing, which also contains a water separator.

DETAILED DESCRIPTION

Figure 1A:
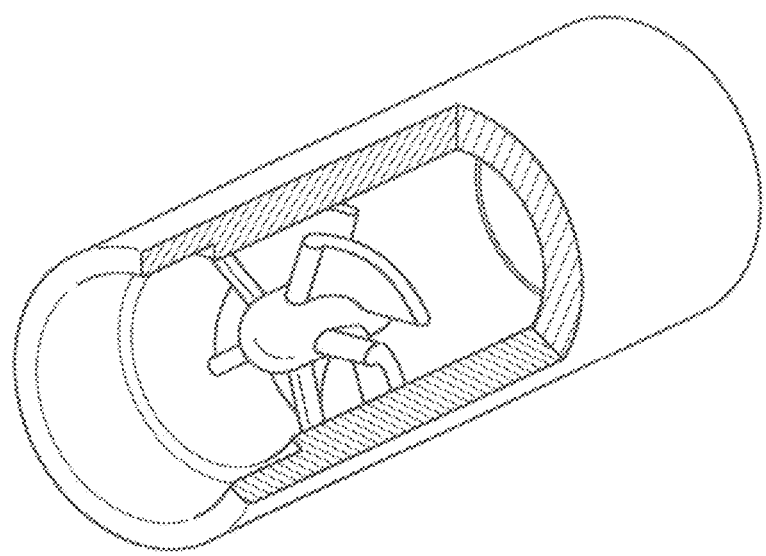
FIG. 1A shows an example of the device in which the interior of the tubular device has arranged an axial flow body with 5 guide vanes.
Figure 1B:
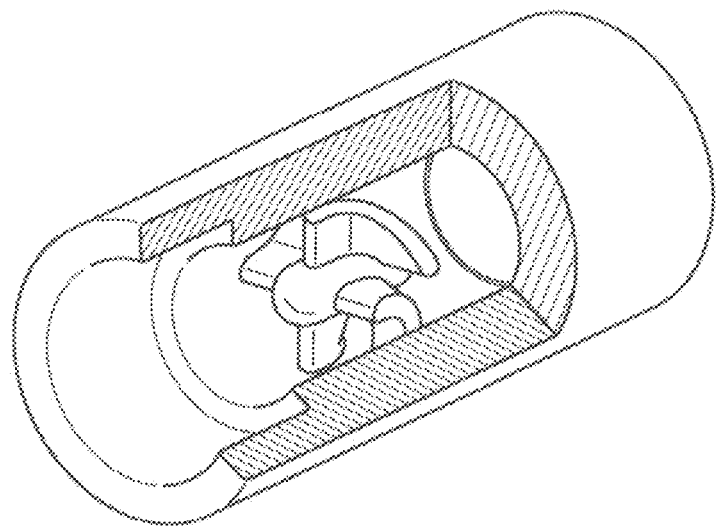
FIG. 1B shows an example of the device in which the interior of the tubular device has arranged an axial flow body with 4 guide vanes is arranged.
Figure 4:
FIG. 4 shows the typical helical separation pattern in the hose.
Figure 5:
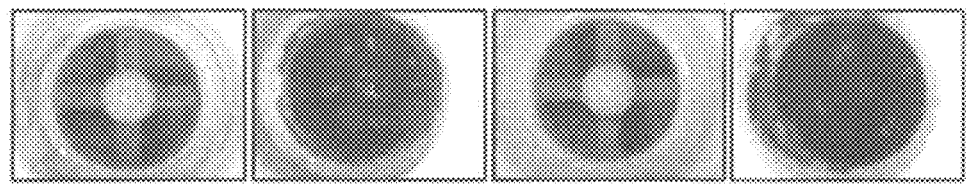
FIG. 5 shows a partial separation will already occur at the outlet opening of the device.

FIGS. 1A and 1B show two examples of devices according to the invention. In either case, the device is configured such that in the interior of the tubular device, an axial flow body with 5 (FIG. 1A) or 4 (FIG. 1B) guide vanes is arranged. The shaft as well as the guide vanes are rigid, the latter are connected to the outer cylinder. When conducting flue gases through the device according to the invention, a separation of liquid and particles occurs in the adjoining hose (see FIG. 4). FIG. 4 also shows the typical helical separation pattern in the hose. Since the spiral turbulence and thus the generated centrifugal forces decrease with increasing distance to the device, the major part of the separation occurs close to the device. A partial separation will already occur at the outlet opening of the device (see FIG. 5).

Figure 3A:
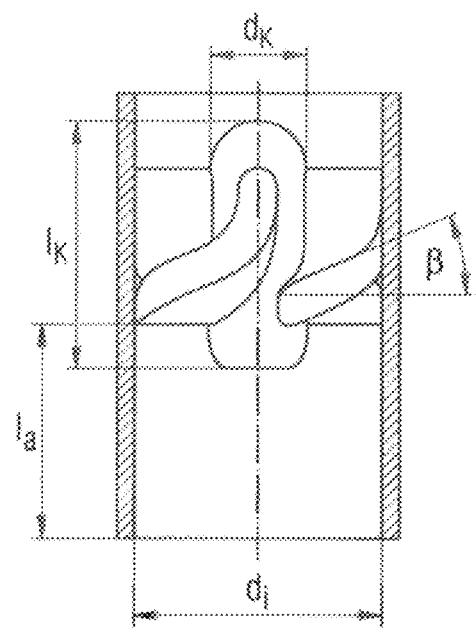
FIG. 3A shows a cross-section of a device.

FIG. 3A shows a cross-section of a device according to the invention. Number and geometry of the device according to the invention are very variable. In general, the inner diameter $d_i$ of the device according to the invention will be in the range from 4 to 20 mm. The diameter of the axial flow body ($d_K$) may be in the range from 0.5 to 6 mm, preferably 1 to 4 mm. According to experience, good separation results are achieved when using 3 to 6 guide vanes. It is, however, also conceivable to provide two helical guide vanes only or more than 6 vanes. The exit angle β of the guide vanes should be between 15 and 30 degrees. It should be noted, here, that the exit angle β needs not be constant over the full radius, but may be variable: It may, for instance, be 30 degrees at the convection to the inner flow body and fall down, in the radial course, to 20 degrees when arriving at the inner wall of the tube.

Figure 3B:
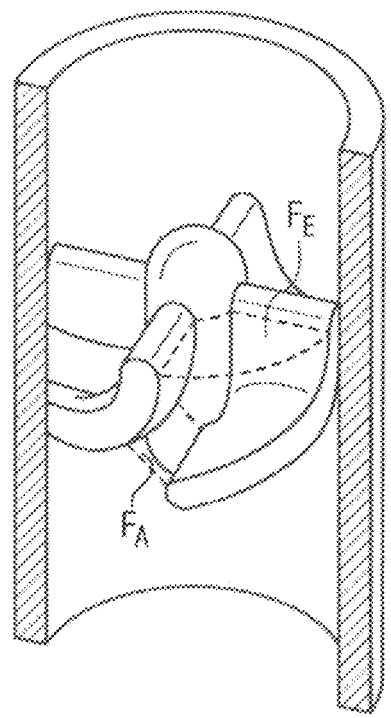
FIG. 3B shows vane entry surface area $F_E$ and the vane exit surface area $F_A$.

FIG. 3B shows the so-called vane entry surface area $F_E$ and the vane exit surface area $F_A$, which play a role for the separation: The ratio S of the surface areas $F_E:F_A$ should be between 1 and 8, preferably between 2 and 5. Particularly preferred is a surface area ratio from 2.7 to 3.3.

In special embodiments, one single guide vane may be sufficient to enable a separation. In this case, the gas flow through the tubular device is separated by a partition wall that is helically arranged in the tube. In order to guarantee the required radial forces, the helical partition wall has to include a rotation by at least 180 degrees, preferably at least 270 degrees, particularly preferably at least 360 degrees.

For the connection of the guide vanes to the axially arranged flow body, there are also different geometries. With a secant-shaped arrangement, there is, in addition to the force ($F_s$) acting perpendicular to the guide vanes, another radial force vector ($F_r$), so that an improved separation performance results.

Figure 2A:
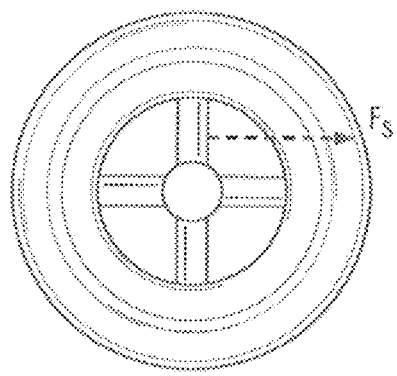
FIGS. 2A and 2B show the connection being orthogonal or secant-shaped for the example of 4 guide vanes.
Figure 2B:
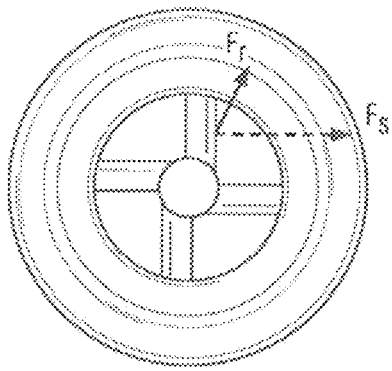

For preferred embodiments of the invention, the following applies:

1. The number of the vanes should be between 3 and 5.
2. The ratio of the length $l_k$ to the web cross-section $d_k$ of the axial body should be between 2 and 3.
3. The ratio of the length behind the guide vanes up to the gas exit $l_a$ to the web cross-section $d_k$ should be between 2 and 4.
4. The ratio S of the vane entry surface area $F_E$ to the vane exit surface area $F_A$ (see FIG. 2) should be between 2.7 and 3.3.

At this point, it should be noted that the device according to the invention has no moving parts and, therefore, can be produced in a simple way. Production may, e.g., be performed by injection molding or 3D printing. In an embodiment of the vanes without undercut, production can be performed by injection molding with a simple and cost-effective open/closed tool. Further improved separation performance is achieved, when the vanes have an undercut. For the production of such devices with an undercut of the vanes, the injection molding production has to be carried out with a spindle insert.

For production by means of 3D printing, all embodiments can be implemented without any particular difficulties.

The device according to the invention may also be integrated in other components of medical devices, as, e.g., in filter housings, hose adapters or the like. The device according to the invention may, if desired, also be combined with other filter devices. The flue gas flow may, for instance, first be directed through a device according to the invention and then through filters of other types (fiber filters, membrane filters, activated carbon filters or the like).

The separation efficiency is also affected by the wall roughness of the downstream hoses and tubes. The higher the roughness of the material, the better is usually the separation. The person skilled in the art is well aware that the roughness can be modified by using corresponding materials, by adaptation of the surface design of the injection molding tool or by surface coatings. Hydrophilic materials and coatings naturally improve in particular the separation of liquid (drop-shaped) flue gas components.

Figure 6:
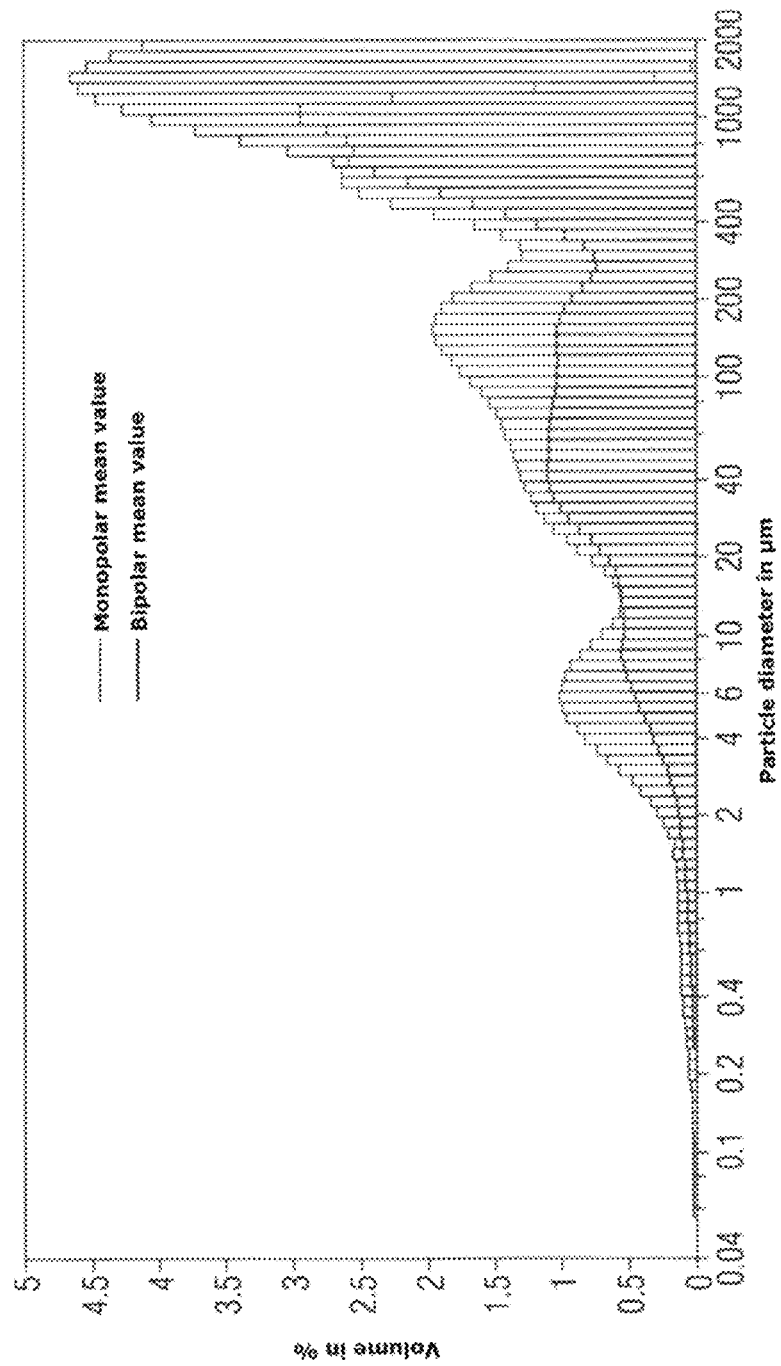
FIG. 6 shows the particle size distribution in typical flue gases in the form of the volume proportion.

FIG. 6 (taken from: Farrugia, M.; Hussain, S. Y. et al. (2009): Particulate Matter Generated During Monopolar and Bipolar Hysteroscopic Human Uterine Tissue Vaporization, in: Journal of Minimally Invasive Gynecology, year 16, No. 4, p. 458-464) shows the particle size distribution in typical flue gases in the form of the volume proportion: It can clearly be seen that the major part of the particles have a size between 2 and 2,000 microns.

FIG. 7 depicts separation curves of the devices shown in FIG. 1 for different gas flows. It can be seen that the separation efficiency clearly increases with the particle diameter and the gas volume flow. Particles > than 1 micron are separated with gas flows between 6 and 12 liters per minute, as they are usual for such medical devices, for 10 to 30 percent already. With particle diameters of 2,000 to 3,000 nanometers (corresponding to 2 to 3 microns), separation occurs under the same conditions for more than 80 percent. Depending on the design of the device and the flow rate, particles with sizes between 100 and 400 nm are also separated, which are only poorly separated by fiber filters.

For gas flows below 6 l/min, particles are only very limitedly separated. Nevertheless, the device according to the invention can also be used with gas flows from 3 to 6 l/min for the separation of humidity.

Figure 8:
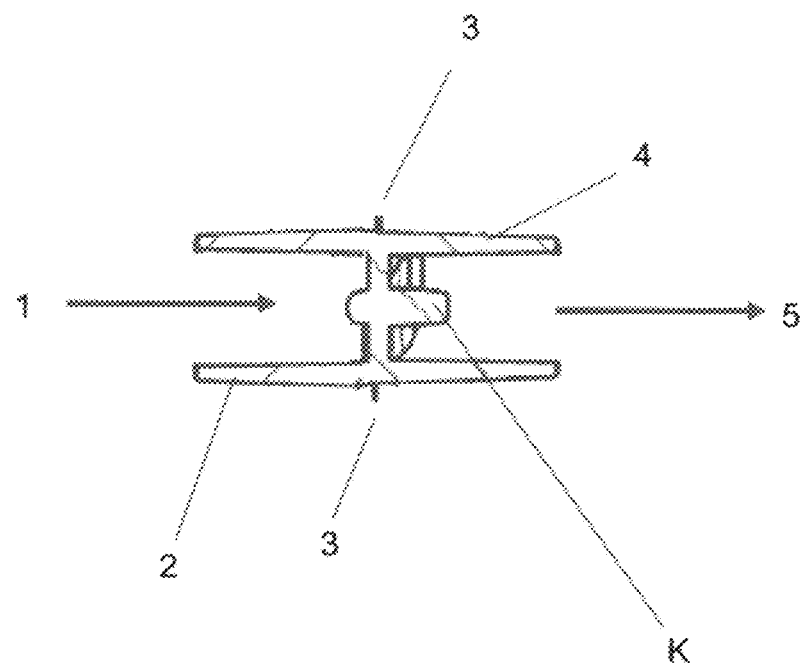
FIG. 8 shows the entry side of the device dimensioned such that a hose can easily be fitted.

As mentioned above, the probably simplest embodiment is to provide the device according to the invention as a hose connector. One possibility for such an embodiment is indicated in FIG. 4. Alternatively, as shown in FIG. 8, the entry side of the device according to the invention is dimensioned such that a hose can easily be fitted. The exterior of the housing (2) may be slightly tapered, in order to enable an easy slip-over. If applicable, the hose may be secured by a hose clamp. The housing may be provided with a central bulge (3). The axial body (K) with guide vanes is located in the interior of the device. On the exit side of the device, there is fitted a second hose and, if applicable, also secured by a hose clamp. In any case, the gas flow coming from the medical suction device (e.g., a laparoscopy device with suction pump) is fed through a first hose to the device according to the invention. When putting the pump into operation, the gas flow is conducted through the first hose into the device and is discharged through the second hose. The gas flow is in the direction of the arrow (1, 5). Particles and humidity also included in the gas flow will deposit in the second hose in characteristic helical areas. The second hose may be made from a different material than the first hose, for instance, having a higher roughness or a more hydrophilic surface, in order to promote the separation.

Figure 9:
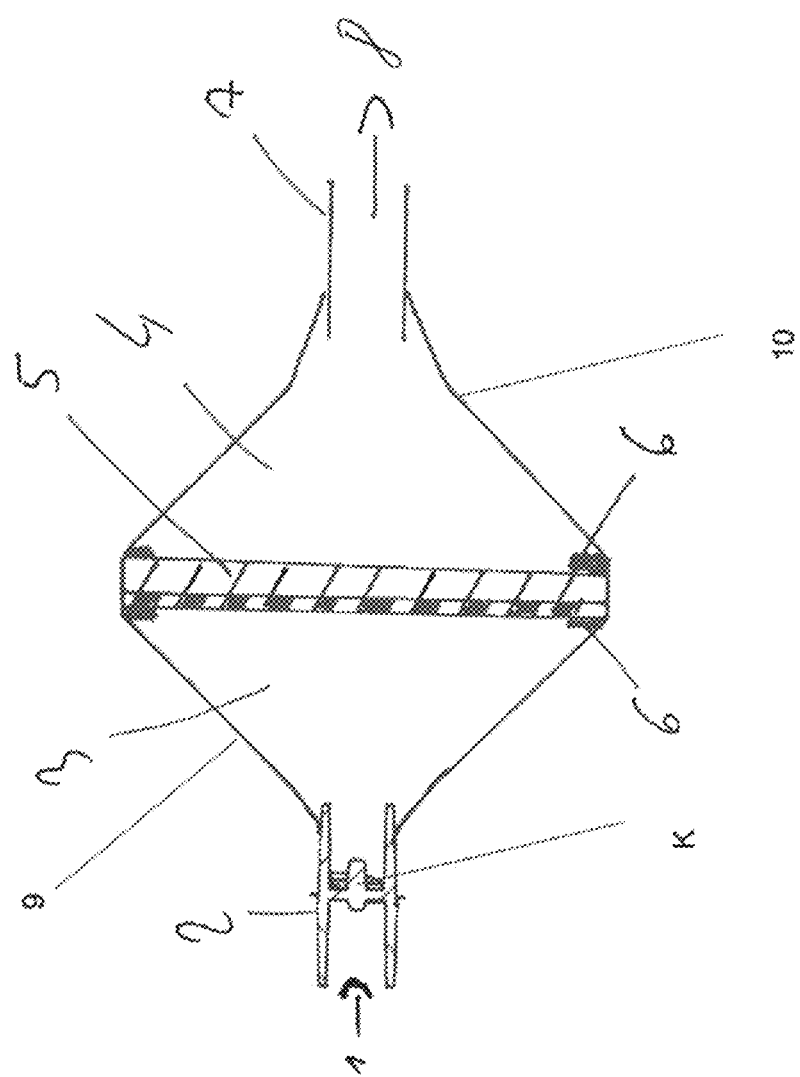
FIG. 9 shows the device integrated in a filter holder.

Another possibility is to integrate the device according to the invention in a filter holder (FIG. 9). Herein, for instance, a filter (5) is held and clamped in a housing, for instance, with corresponding clamping elements (6). The housing consists, for instance, of two cone-shaped parts (9, 10), with the two cone bottoms, for instance, being connected to each other by a bayonet coupling. The filter may consist of two layers, and in addition to the fiber filter, an activated carbon filter may be provided. The latter may be connected in a sheet-like manner to the fiber filter or may be integrated in a tubular manner in the housing outlet (not shown). In the inlet of the housing, the device according to the invention with the axial body (K) and integrally formed guide vanes is integrated. The outlet port of the device is simultaneously the entry of the gas flow into the first chamber (3). After passage through the filter (5), the gas flow is guided to the housing outlet (7). In this embodiment, the filter size is usually much larger than the diameter of the outlet port, in order to prevent clogging of the filter. With a diameter of the outlet port of 20 mm, a filter area of 30 to 100 cm$^2$ is recommended, and it does not matter, whether the filter area is round, square, rectangular, or has a different geometry.

In another possible embodiment of the invention (FIG. 10), the device according to the invention is integrated in a filter housing, which also contains a water separator. The housing (10) comprises a first chamber (3), into which the outlet port of the device according to the invention (2) with an axial body (K) and guide vanes opens out, and which thus forms the gas entry into the first chamber. The first chamber (3) includes a gas exit (7). The gas exit (7) may be arranged in line with the gas entry. As shown in FIG. 10, in special embodiments the gas exit may also be arranged offset with respect to the gas entry. In order to enable the desired water separation without water entering the second chamber (4), it is recommended in this case to provide the socket-type exit at a higher level than the entry. The gas flow coming from the device according to the invention hits in this case on the rear wall of the chamber (5), where liquid drops can be deposited. The bottom of the first chamber may be made of a humidity-absorbing material (6) (e.g., superabsorber). The exit socket (7) integrated in the rear wall leads into a second chamber (4) that is provided with a filter arrangement (11). The filter arrangement (11) may, for instance, consist of a fiber filter for the separation of remaining particles possibly still present in the gas flow, and of an activated carbon filter for the separation of gases (e.g. HCN, CO, $SO_2$). In this case, too, a large-area filter arrangement is recommended, for preventing clogging of the filter. The gas flow filtered by this overall arrangement leaves the second chamber through an exit socket (12). The gas flow through the overall arrangement follows the direction of the arrows (1, 8, 9).

Summarizing, the invention has succeeded in providing a simple device that can be manufactured at reasonable cost, can easily be integrated in existing medical systems, e.g., medical insufflation devices with suction system, and nevertheless enables an efficient separation of particles and liquid droplets from flue gases. The cost-effective production permits the use for one single application, so that expensive cleaning and sterilization processes, as they are typical for surgical applications, can be avoided.

The invention claimed is:

1. A device for the separation of particles, drop-lets, and humidity from flowing flue gases having a flow rate of 3 to 20 l/min,
comprising a tube of length 1 of 10 to 50 mm, the tube having an inner diameter di of 4 to 20 mm,
comprising an axially located flow body K having a web cross-section of 0.5 to 6 mm,
comprising two to six guide vanes L disposed between the axially located flow body K and the inner wall of the tube, the guide vanes L being rigidly connected to the inner wall of the tube,
wherein the guide vanes L are helically arranged so as to confer a radial movement component to the gas flowing through, the guide vanes having a ratio S of a vane entry surface area FE to a vane exit surface area FA of between 2.7 and 3.3;
wherein the vane entry surface are FE defines an effective flow cross-section at an inlet to the guide vanes and the vane exit surface area $F_A$ defines a flow cross-section at an outlet from the guide vanes.

2. The device according to claim 1 comprising 3 to 5 guide vanes L.

3. A method for the separation of flue gas particles and liquid droplets in the exhaustion of surgical gases in medical devices which comprises utilizing the device of claim 2.

4. The device according to claim 1, wherein the guide vanes have an exit angle β between the axially located flow body K and the tube cross-section of 20 to 30 degrees.

5. A method for the separation of flue gas particles and liquid droplets in the exhaustion of surgical gases in medical devices which comprises utilizing the device of claim 4.

6. The device according to claim 1, wherein the ratio of a length lk of the axial flow body to the web cross-section of the axial flow body dK is between 2 and 3.

7. A method for the separation of flue gas particles and liquid droplets in the exhaustion of surgical gases in medical devices which comprises utilizing the device of claim 6.

8. The device according to claim 1, wherein the ratio of a length la between the last edge of the guide vane, in the direction of flow, and a tube exit to the web cross-section of the axial flow body dK is between 2 and 4.

9. A method for the separation of flue gas particles and liquid droplets in the exhaustion of surgical gases in medical devices which comprises utilizing the device of claim 8.

10. The device according to claim 1, wherein the connection between the axial flow body and the guide vane is orthogonal or secant-shaped.

11. A method for the separation of flue gas particles and liquid droplets in the exhaustion of surgical gases in medical devices which comprises utilizing the device of claim 10.

12. The device according to claim 1, wherein the tube with flow body and guide vanes is integrated in a housing in which particles, liquids and/or gases are separated.

13. The device according to claim 12, further comprising a fiber filter, a humidity-absorbing material and activated carbon, wherein particles are separated by the fiber filter, water is separated by the humidity-absorbing material gases are separated by the activated carbon.

14. A method for the separation of flue gas particles and liquid droplets in the exhaustion of surgical gases in medical devices which comprises utilizing the device of claim 13.

15. A method for the separation of flue gas particles and liquid droplets in the exhaustion of surgical gases in medical devices which comprises utilizing the device of claim 12.

16. A method for the separation of flue gas particles and liquid droplets in the exhaustion of surgical gases in medical devices which comprises utilizing the device of claim 1.

17. The device according to claim 1 wherein the guide vanes having a ratio S of a vane entry surface area $F_E$ to a vane exit surface area $F_A$ of between 2 and 5.

* * * * *